(12) United States Patent
Wilson et al.

(10) Patent No.: US 9,044,179 B2
(45) Date of Patent: Jun. 2, 2015

(54) OXYGEN SENSOR FOR INTERNAL MONITORING OF TISSUE OXYGEN IN VIVO

(75) Inventors: David F. Wilson, Philadelphia, PA (US); Gregory J. Schears, Rochester, MN (US)

(73) Assignee: The Trustees of the University of Pennslyvania, Philadelphia, PA (US)

(*) Notice: Subject to any disclaimer, the term of this patent is extended or adjusted under 35 U.S.C. 154(b) by 1330 days.

(21) Appl. No.: 12/087,391

(22) PCT Filed: Jan. 4, 2007

(86) PCT No.: PCT/US2007/000292
§ 371 (c)(1),
(2), (4) Date: Nov. 12, 2008

(87) PCT Pub. No.: WO2007/081811
PCT Pub. Date: Jul. 19, 2007

(65) Prior Publication Data
US 2009/0216097 A1    Aug. 27, 2009

Related U.S. Application Data

(60) Provisional application No. 60/756,112, filed on Jan. 4, 2006.

(51) Int. Cl.
*A61B 5/1459* (2006.01)
*A61B 5/145* (2006.01)
(Continued)

(52) U.S. Cl.
CPC ........... *A61B 5/14542* (2013.01); *A61B 5/0059* (2013.01); *A61B 5/1455* (2013.01);
(Continued)

(58) Field of Classification Search
CPC ............. A61B 5/14532; A61B 5/1459; A61B 5/14552; A61B 5/14551
USPC .................. 128/204.22; 250/580, 581, 458.1; 356/948, 950, 951; 436/68; 600/309–312, 317, 323–327, 329, 337, 600/339–342, 364
See application file for complete search history.

(56) References Cited

U.S. PATENT DOCUMENTS 3,787,119 A    1/1974    Rybak
3,814,081 A    6/1974    Mori
(Continued)

FOREIGN PATENT DOCUMENTS

EP    0352610    1/1990
WO    WO 90/06718    6/1990
WO    WO 98/26709    6/1998

OTHER PUBLICATIONS

Lo et al., "Calibration of Oxygen-Dependent Quenching of the Phosphorescence of Pd-meso-tetra (4 Carboxyphenyl) Porphine: A Phosphor with General Application for Measuring Oxygen Concentration in Biological Systems." Analy. Biochem. 236:153-160 (1996).

(Continued)

*Primary Examiner* — Melanie Yu Brown
*Assistant Examiner* — Erik B Crawford
(74) *Attorney, Agent, or Firm* — Riverside Law LLP (57) ABSTRACT

Provided is a durable oxygen sensitive probe of sufficient strength to withstand direct tissue pressures in vivo, the probe comprising a sensor chamber within a biocompatible, gas-permeable membrane containing an oxygen sensitive analyte solution producing oxygen quenchable phosphorescence when excited. Further provided is a tissue oxygen detection and measurement system comprising the probe, and methods for use of the probe and the system to directly, rapidly and accurately measure tissue oxygen levels in a patient without reliance on blood vessels or fluid protection of the probe.

25 Claims, 1 Drawing Sheet

(51) Int. Cl.
  *A61B 5/00* (2006.01)
  *A61B 5/1455* (2006.01)
  *G02B 6/032* (2006.01)

(52) U.S. Cl.
  CPC ......... *A61B 5/14551* (2013.01); *A61B 5/14552* (2013.01); *A61B 5/6846* (2013.01); *G02B 6/032* (2013.01); *G02B 2006/0325* (2013.01); *A61B 5/14539* (2013.01); *A61B 5/1459* (2013.01)

(56) References Cited

U.S. PATENT DOCUMENTS

| | | | |
|---|---|---|---|
| 4,200,110 A | 4/1980 | Peterson | |
| 4,476,870 A | 10/1984 | Peterson | |
| 4,752,115 A | 6/1988 | Murray | |
| 4,758,814 A | 7/1988 | Howng | |
| 4,947,850 A | 8/1990 | Vanderkooi | |
| 5,018,209 A | 5/1991 | Bacus | |
| 5,127,405 A | 7/1992 | Alcala | |
| 5,219,527 A * | 6/1993 | Hui et al. | 422/82.06 |
| 5,353,792 A * | 10/1994 | Lubbers et al. | 600/311 |
| 5,501,225 A | 3/1996 | Wilson | |
| 5,593,899 A | 1/1997 | Wilson | |
| 5,782,804 A | 7/1998 | McMahon | |
| 5,830,138 A | 11/1998 | Wilson | |
| 6,274,086 B1 | 8/2001 | Wilson | |
| 6,285,807 B1 * | 9/2001 | Walt et al. | 385/12 |
| 6,362,175 B1 | 3/2002 | Vinogradov | |
| 2006/0129041 A1 * | 6/2006 | Ellis et al. | 600/341 |

OTHER PUBLICATIONS

Pawlowski et al., "Monitoring Of The Oxygen Pressure In The Blood Of Live Animals Using The Oxygen Dependent Quenching Of Phosphorescence." Adv. Exp. Med. Biol. 316:179-185 (1992).

Robiolio et al., "Oxygen diffusion and mitochondrial respiration in neuroblastoma cells." Am. J. Physiol. 256 (6 Pt 1): C1207-1213 (Jun. 1989).

Vanderkooi et al., "An Optical Method for Measurement of Dioxygen Concentration Based upon Quenching of Phosphorescence." J. Biol. Chem. 262(12):5476-5482 (Apr. 1987).

Vanderkooi et al., A New Method for Measuring Oxygen Concentration of Biological Systems, in Oxygen Transport to Tissue VIII, Longmuir, ed., Plenum (Aug. 1986).

Vinogradov et al., "Metallotetrabenzoporphyrins. New Phosphorescent Probes for Oxygen Measurements." J. Chem. Soc., Perkin Trans. 2:103-111 (1995).

Wilson et al., "The Oxygen Dependence of Mitochondrial Oxidative Phosphorylation Measured by a New Optical Method for Measuring Oxygen Concentration." J. Biol. Chem., 263:2712-2718 (1988).

Wilson et al., "Effect of Hyperventillation on Oxygen of the Brain Cortex." Adv. Exp. Med. Biol. 316:341-346 (1992).

Written Opinion for European Application 07716364.0.

\* cited by examiner

OXYGEN SENSOR FOR INTERNAL MONITORING OF TISSUE OXYGEN IN VIVO

REFERENCE TO RELATED APPLICATIONS

This patent application claims priority to Provisional Application 60/756,112, filed Jan. 4, 2006 and PCT Application PCT/US2007/000292, filed Jan. 4, 2007, which is herein incorporated in its entirety.

FIELD OF THE INVENTION

The present invention provides an improved system for measuring tissue oxygen partial pressure (concentration). Further provided is an improved optical probe for directly using this system to measure tissue oxygen of a patient without requiring delivery of the sensor to the lumen of a blood vessel.

BACKGROUND OF THE INVENTION

The present invention is based upon the phenomenon that oxygen has a quenching effect on the molecular luminescence of various chemical compounds and that this effect can be employed for imaging oxygen concentrations (partial pressure) in vivo. Animals, especially mammals, are dependent upon having adequate oxygen supplies in their body tissues. In mammals, the circulatory system employs specialized oxygen-carrying molecules in the blood to deliver oxygen from the lungs to other tissues throughout the body. Thus, every organ in the body contains oxygen in varying amounts and concentrations in every tissue, and information regarding the distribution and concentration of oxygen in tissue can be indicative of structure, anomalies, defects or disease.

For example, in traumatic injury, the primary threat to life is often the loss of blood and the resulting hemorrhagic shock and hypotension, under-perfusion of tissue and abnormal the blood flow among and within the tissues. As a result, regions of tissue become hypoxic, or relatively devoid of oxygen. Loss of blood volume is usually treated by plasma expanders, in an effort to maintain blood pressure, and to improve oxygen delivery to the tissue until surgery can be performed, and following repair, oxygen levels can offer a measure of efficacy. See, for example, U.S. Pat. Nos. 5,593,899 and 4,947,850 which disclose methods and apparatus for imaging internal body structures and measuring oxygen dependent quenching of phosphorescence.

Fiber-optic sensors have been used to measure oxygen levels in vivo by positioning an analyte-sensitive indicator molecule in a light path at a desired measurement site. Typically, the optical fiber transmits electromagnetic radiation from a light source to the indicator molecule, and the reflectance from or absorption of light by the indicator molecule gives an indication of the gaseous or ionic concentration of the analyte. Alternatively, for monitoring an analyte, such as oxygen, the optical fiber transmits electromagnetic radiation to the indicator molecule, exciting it into a type of luminescence, i.e., phosphorescence, and the level and/or duration of phosphorescence by the indicator molecule serves as an indication of the concentration of the gas in the surrounding fluid. In the prior art sensors, the indicator molecules are typically disposed in a sealed chamber at the distal end of an optical fiber, and the chamber walls are permeable to the analytes of interest.

Several sensor devices are known which are useful for measuring oxygen and pH content in human and animal tissues by insertion of a light-sensing, optical fiber probe into a blood vessel of the subject. See, for example, U.S. Pat. No. 5,830,138 providing a detection device for measuring tissue oxygen and/or pH($CO_2$) via insertion of a probe into a blood vessel of a subject in vivo, wherein the probe comprises a fiber optic means enclosed within a gas-permeable film. Situated between the gas-permeable film and the fiber optic means is a reservoir of a liquid, containing an aqueous oxygen-quenchable, phosphorescence-emitting oxygen sensor and/or a fluorescence-emitting pH sensor, and further comprising a means for detecting phosphorescent and/or fluorescent excitation light.

U.S. Pat. No. 4,758,814 provides an optical fiber covered by a membrane constructed of a hydrophilic porous material containing a pH sensitive dye for measuring blood pH levels, and having embedded in the membrane several hydrophobic microspheres containing a fluorescent dye quenchable by oxygen to simultaneously or sequentially measure oxygen partial pressure. Another fluorometric oxygen sensing device is described in U.S. Pat. No. 5,012,809, wherein the fluorometric sensor is constructed with silicone polycarbonate bonded to one or more plastic fiber optic light pipes using polymethylmethacrylate glues. U.S. Pat. No. 5,127,405 provides another version of a fiber optic probe containing an oxygen-permeable transport resin embedded with a luminescent composition comprising crystals of an oxygen quenchable phosphorescent material, whereby frequency domain representations are used to derive values for luminescence lifetimes or decay parameters. U.S. Pat. No. 4,752,115 employs an optical fiber, 250 nm in diameter or small enough for insertion into veins and/or arteries, wherein the probe is coated with an oxygen sensitive (oxygen quenchable) fluorescent dye which fluoresces light back to measure regional oxygen partial pressure, and wherein the oxygen sensing end of the probe may further include a gas-permeable sleeve over the optical fiber.

U.S. Pat. No. 4,476,870 discloses a fiber optic probe for implantation in the human body for gaseous oxygen measurement in the blood stream by means of a probe employs oxygen quenchable dye fluorescence enveloped in a hydrophobic, gas-permeable material at the end of two 150 um strands of a plastic optical fiber. U.S. Pat. No. 4,200,110 discloses a fiber optic pH probe employing an ion-permeable membrane envelope enclosing the ends of a pair of optical fibers, with a pH sensitive dye indicator composition disposed within the envelope. U.S. Pat. Nos. 3,814,081 and 3,787,119 describe early versions of such probes using photosensitive cells to determine physical and chemical characteristics of blood in vivo by direct measurement of light, but without oxygen quenchable phosphor/fluorophor compounds.

However, while the prior art probes are intended for measuring "tissue oxygen" in a patient in vivo, they require insertion into the lumen of a blood vessel and actually measure blood gases, not oxygen in the tissue surrounding the vessel. Blood flow rapidly changes the oxygen level within a given point in the vessel and would offer no way of measuring tissue oxygen in, for example, necrosing tissue. Nor can the prior art systems be effective in regions not supplied with large vessels, such as muscle tissue, or in damaged tissue areas where the blood vessels are no longer intact, as in emergency situations.

One structural problem with the prior art sensing systems of the type described for use in blood vessels, is that the structure of the chambers and probe configuration often encourage the formation of blood clots or thrombi. Particularly when multiple fibers are used to determine several blood gas parameters, such as oxygen, carbon dioxide, and pH together, the probe provides interfiber crevices that encourage thrombi formation. Furthermore, the complexity and difficulty of manufacturing multi-fiber probes is well known, due to the small diameters of the fibers and requirements of their arrangement. Such probes must be small enough to fit within a blood vessel while still permitting blood to flow, especially problematic for neonatal or pediatric applications in which the patient's veins or arteries may be too small in diameter for insertion of the probe assembly.

Moreover, correctly placing the sensing end of the probe in the blood vessel and maintaining that placement for continued monitoring is important for obtaining reliable blood gas results. The prior art tissue oxygen or multianalyte sensors have failed to effectively deal with the problems set forth above, and none offer a method for measuring oxygen in tissue other than via a blood vessel.

The design of the prior art probes is distinctly different from a device that can directly measure analyte levels in tissue, although similar sensor compositions and detection monitors may be used. A tissue probes that is not protected by a blood vessel, must withstand much higher local tissue pressures. For example, if prior art probes were inserted directly into tissue, rather than into a blood vessel, they would collapse or be disabled under the pressure of the surrounding tissue. They lack sufficient wall strength to withstand tissue pressure without the protection of a blood vessel and a surrounding fluid environment. Consequently, without the protection by the blood and blood vessel, insertion of a prior art probe directly into a non-fluid, tissue environment could compress and damage the sensor chamber, resulting in failure or a significantly decreased excitation of a phosphor sensor, as well as decreased collection of the returned phosphorescent excitation light. Side pressures could further cause sharp bends or "kinks" immediately adjacent to the optical fibers, which must be accounted for in the probe design.

Thus, until the present invention there has remained a need in the art to provide an improved device and method for directly, rapidly and accurately measuring oxygen levels in tissue, particularly in vivo. However, such information would be highly beneficial as a diagnostic tool, and would facilitate the quick, accurate and precise identification of many otherwise difficult-to-diagnose maladies or detecting life-threatening situations.

SUMMARY OF THE INVENTION

In accordance with the present invention, oxygen measurements in tissue take advantage of novel phosphors which absorb and emit light in the near infra red region of the spectrum. A probe containing the sensor of the present invention is distinguished from the prior art in that it is place directly into the patient's tissue; it is not delivered into the body via the lumen of a blood vessel. As a result, the device, system and methods of the present invention directly measure tissue oxygen in the capillary bed of the selected tissue; this is not a measure of blood gases within a vessel. In use, the probe of the present invention is not protected by the blood vessel and surrounding fluids, thus the design is necessarily different from prior art technologies that operate from within a blood vessel. In accordance with the present invention, the tissue oxygen levels may be read directly.

The unique design and placement within the tissue, particularly effective within muscle tissue, permits the oxygen probe to be rapidly inserted in a matter of seconds, even under difficult conditions, such as those often faced by first medical responders. Once in place, the probe provides immediate data regarding cardiac and pulmonary function (tissue oxygen) to facilitate rapid and accurate treatment of the patient.

Thus, the present invention provides a device and system for detecting and directly measuring oxygen in tissue of a patient (without reliance on an adjacent blood vessel or fluid environment), wherein the device comprises a sensor chamber enclosed within a gas-permeable layer, the sensor containing an analyte solution, comprising an oxygen quenchable aqueously-soluble, phosphorescence-emitting oxygen sensor, wherein refractive index of the analyte solution in the sensor chamber is higher than that of the surrounding gas permeable layer; a light source for transmitting controlled excitation light to the analyte; and a detecting device for detecting light emitted from the excited analyte. The component comprising the sensor chamber and analyte within a gas permeable layer are referred to as the "tissue probe." The tissue probe device combined with the excitation and detection means form the "system" of the invention. The volume of the tissue area that can be analyzed by a probe is typically a three-dimensional region measuring at least about 5-10 mm on a side.

It is a further object of the invention to provide a tissue probe for use in the system as described, which is effectively used directly in the tissue of a patient without requiring the protection and limitations of insertion into the patient via a blood vessel. In one aspect of the invention, the probe comprises an oxygen-quenchable phosphorescence emitting compound (hereinafter "phosphor," also referred to herein as the "analyte") dissolved in solution in an aqueous solvent within the sensor chamber. In contrast to the prior art in this area, when a probe is used in a vein or artery, it must be less 200-300 µm in diameter to permit passage into the lumen of the vessel, whereas the present invention is not so limited, providing distinct advantages over intravascular prior art devices.

It is also an object of the invention to provide a system comprising the probe, operably attached to one or more optic fibers having two opposing ends. For discussion purposes, the device of the present invention embodied with optic fibers for transmitting light has a proximal end and a distal end. The distal end of the device comprises the probe containing the sensor chamber that is inserted into the patient's tissue in accordance with recognized medical practices. The distal end(s) of the fiber(s) are connected to, and form, a tight and durable seal with the probe. These distal end(s) of the optical fiber(s) are further enclosed within a tube of a gas-permeable layer extending from the layer enclosing the sensor, thereby forming a light guide. The phosphorescence provided when the phosphor is excited has substantially the same refractive index as the optical fibers. At least one of the fibers transmits excitation light from an external light source at the proximal end of the optical fiber(s) to the phosphorescent analyte. Conversely, at least one fiber collects emitted light from the analyte and transmits the collected, emitted light to an external detector device, which is also connected to the proximal end of the fiber(s). Thus, at the proximal end of the optical fiber(s) are the light source and detection components of the system external to the point of entry into the patient or extending externally beyond the point of entry.

Further provided are embodiments wherein the probe is inserted into the patient's tissue as described, but the excitation light is provided transdermally from outside of the patient to the probe without an optical fiber connection. Similarly, the collection and detection of the phosphorescence can be conducted transdermally from outside of the patient without an optical fiber connection.

In yet another alternative embodiment of the invention, it is a further object to provide a fluorescence emitting compound (hereinafter a "fluorophor") within the sensor chamber of the tissue probe to detect and measure pH($CO_2$ levels) and/or $K^+$ ion levels of the tissue. Such alternative embodiments may be combined with or used in addition to the phosphor sensor of the present invention, but would be activated and measured in the same manner as is described in detail for the phosphors.

Further, in accordance with the invention, light-emitting diodes are used for excitation of the phosphorescence, thereby taking advantage of their ability to provide a bright monochromatic light source which can easily be modulated at the required frequency and with the desired waveform.

Additional objects, advantages and novel features of the invention will be set forth in part in the description, examples and figures which follow, and in part will become apparent to those skilled in the art on examination of the following, or may be learned by practice of the invention.

DETAILED DESCRIPTION OF CERTAIN EMBODIMENTS OF THE INVENTION

The present invention comprises a system and device for directly detecting and measuring tissue oxygenation, without using a blood vessel to deliver the sensor probe to the region of interest. In the present invention, measurements are not made in a fluid or blood within a blood vessel, although the tissue may itself be, and likely is, vascularized. Living tissues in the body of a patient are, indeed, vascularized, being richly supplied with capillaries. Many of the sensor, detection, and information recording components disclosed in U.S. Pat. No. 5,830,138 may be adapted for use in the present invention, and it is entirely incorporated by reference herein. Nevertheless, the present system, and probe and methods of its operation are neither the same as the intra-vessel detection method of the '138 patent, nor does the present device require placement within the lumen of a vessel. The present invention is not intended for measuring arterial or venous blood gases. Thus, it is not limited as is the '138 invention, which requires insertion of the probe into a blood vessel. Nor is the present invention intended to operate in a fluid environment, such as within blood in a blood vessel. To the contrary, the embodied tissue probe is specifically designed and intended to withstand the compression of surrounding tissue, including dense muscle tissue, without damage, alteration or collapse of the probe or the sensor chamber contained therein.

The basic embodiment of the tissue oxygen measuring system of the present invention comprises a sensor chamber containing a solution of an oxygen-sensitive phosphor analyte within a biocompatible, gas-permeable membrane that quickly permits the analyte to assume the same oxygen concentration as the surrounding tissue. All devices for exciting the phosphor, and for reading the phosphorescence produced to determine the oxygen levels in the tissue may be activated and utilized, transdermally or by optical fiber connection, from outside of the patient. Eventually, as diodes become smaller (<2 volts), the excitation light source may be self-contained and included within the probe end, rather than external to the patient. Such use of an internal excitation light source is further encompassed by the present invention.

Figure 1:
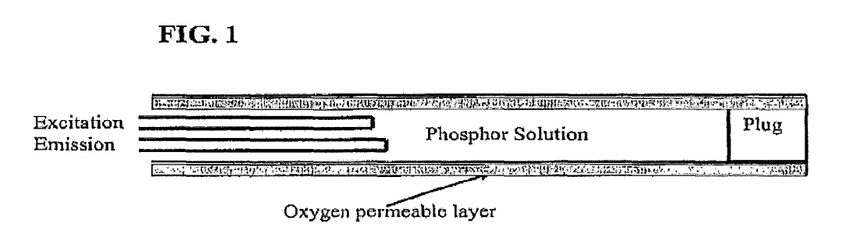
FIG. 1 depicts an embodiment of the invention showing a side-view cross-section of the sensor end of the probe showing a single optical fiber for transmitting excitation light and one for collecting emitted phosphorescence.
Figure 3:
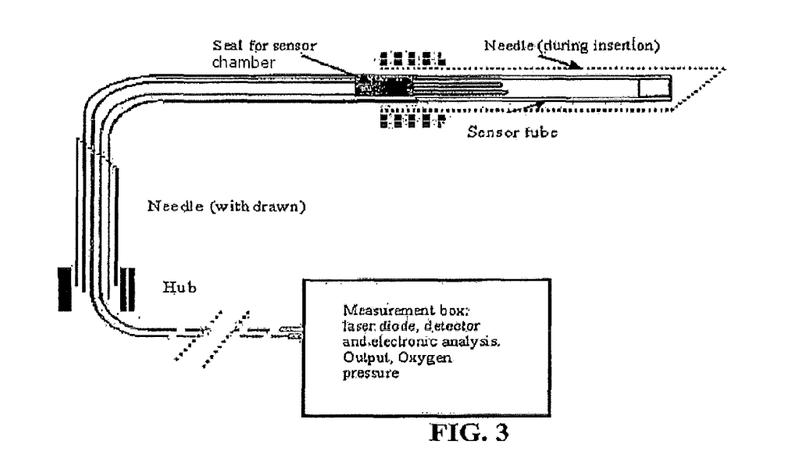
FIG. 3 depicts an embodiment of the invention showing a side-view cross-section of the system including the probe of FIG. 1 attached to the excitation and detection devices by one or more optical fibers, and showing the retractable needle in its retracted position. The drawing is not to scale and as show by the cuts in the optical fibers, they can be of any length.

In a preferred mode of the current invention, the probe containing the sensor chamber and analyte(s) is operably connected to optical fibers for conducting the excitation light to the phosphor, and for conducting the oxygen-quenched phosphorescence from the excited phosphor to the detector. FIGS. 1 and 3. Although surgical placement may be used, the probe is at its simplest and most useful form for emergency situations when it follows into the tissue behind a retractable insertion needle. Moreover, this needle must be retractable to place the sensor chamber in direct contact with the surrounding tissue. FIG. 3. The sensor chamber is smaller in diameter than the retractable needle. In addition, in most applications, the sensor can be quite short (~1-2.5 cm in length), since it is only inserted a short distance into the tissue, typically to depths of not more than 2-3 inches. For resuscitation applications, the sensor would only need to be inserted so that the outermost end is within 3 mm deep into the tissue. In other applications, the length may be much greater.

Figure 2:
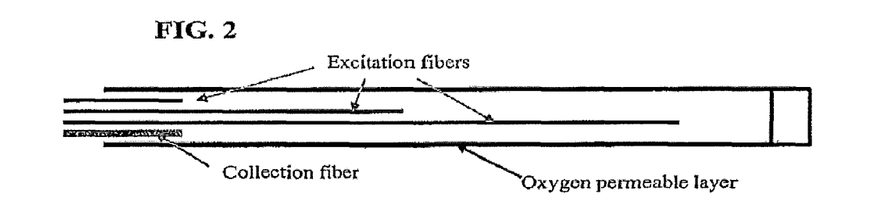
FIG. 2 depicts an embodiment of the invention showing a side-view cross-section of the sensor end of the tube showing multiple optical fibers for transmitting excitation light.

Tissue depth, however, should not be considered to be a limitation or requirement of the invention since alternative embodiments, for example comprising multiple sensor units, as will be described, could contain a plurality of sensors chambers distributed along the length of the fibers or at one or more points other than the distal tip of the fiber, allowing multiple measurements sequentially or simultaneously. Multiple optical fibers as shown in FIG. 2 may also be applied in the present invention to enhance and distribute the excitation light provided to the phosphor. In contrast to intravascular systems, e.g., the '138 patent, the entire length of the apparatus in the body must be covered with a catheter because it is exposed to the blood in the vessel. While the present invention does not require such a covering, it would, for example, be possible to coat the fiber optics with a sterile and sterilizable composition.

The "patient" of the present invention is any human or animal into which tissue oxygen measurement would be useful. The patient can be healthy or diseased, and be of any age or size, from neonates to adults. All will benefit from the advantages of the rapid and accurate measurement of tissue oxygen provided by the present invention.

1. System for Measuring Tissue Oxygen

An embodied system of the present invention comprises a biocompatible, gas-permeable layer-enclosed sensor chamber containing an aqueous phosphor analyte, which rapidly, in less than 15 seconds, equilibrates with the tissue oxygen of the surrounding tissue. When the phosphor is excited by a light source to phosphoresce, the level of resulting phosphorescence is modulated by the presence of oxygen in the surrounding tissue (oxygen-quenching is a well known characteristic of phosphorescence). Relying upon known physical properties of the selected phosphor, the oxygen-quenched phosphorescence lifetime of the analyte provides a highly accurate and direct measurement of the tissue oxygen level in the surrounding tissue. A laser diode, which in certain embodiments is coupled into an optical fiber (6 to 250 micron core diameter), is preferably used for excitation of phosphorescence in a phosphor sensor of the probe. A light sensitive detector (photomultiplier, avalanche photodiode or silicon photodiode) is used to measure the emitted phosphorescence.

The detector is preferably covered with an optical filter to exclude light of all wavelengths other than that of the emitted phosphorescence. In particularly, the wavelength(s) of the excitation light is excluded from those wavelengths that are detected. The laser diode applies light, either in short pulses (time domain measurement of lifetime) or modulated at differing frequencies (frequency domain measurement of lifetime). In each case, the detected phosphorescence signal, fitted to a single exponential or the phase shift relative to the excitation light, is determined and used to calculate the oxygen concentration in the tissue.

The measured phosphorescence lifetime values are then used to calculate oxygen pressure from the Stern-Volmer relationship $\tau_o/\tau = 1 + k_q \cdot \tau_o \cdot PO_2$ as described in greater detail in Equation 1 below. The values for $\tau_o$ and $k_q$ for the phosphor are determined by calibration of the phosphorescence lifetime at the temperature of the measurement.

The present system, therefore, comprises all of the elements necessary for measuring tissue oxygen: the sensor probe including the gas-permeable layer and the analyte, a light source, a photodetector, and further in the case of the system using optical fibers, one or more optical fibers operably connected to deliver excitation light from the light, and for collecting and delivering phosphorescence to the photodetector from which oxygen pressure can be calculated based on the oxygen quenching of the analyte activity.

2. Optical Fibers

In certain embodiments of the invention, one or more optic fibers are used to provide light transmission through flexible transmission fibers to direct the light to the distal end of the sensor probe. In that case, the wave-guide is a single optical fiber or several single fibers, or a bundle of light conducting fibers, or any combination thereof (collectively referred to herein simply as an "optical fiber"). The amount of light that will enter the fiber is a function of several factors: the intensity of the light source (e.g., LED or LD), the area of the light emitting surface, the acceptance angle of the fiber, and the losses due to reflections and scattering. As the term is typically used, each optical fiber comprises a light carrying core and cladding which traps light in the core. Usually each fiber is a two-layered, glass or plastic structure, with a higher refractive index interior covered by a lower refractive index layer. One of ordinary skill in the field of fiber optics would be familiar with, and could readily select from, the range of construction types, from continuous gradient to steps in refractive index. If cladded it would be specifically adapted for the present invention, as in a permeable, but reflective, plastic film layer.

The optical fibers for conducting the excitation light to the phosphor and for conducting the phosphorescence from the phosphor to the detector are connected to the phosphorescence lifetime measuring instrument through, e.g., a dual channel quick connect port, making the light guide element easily connected and disconnected from the phosphorescence lifetime measuring instrument. See FIG. 3. The term "light guide," used interchangeably with wave-guide or optical-guide, and spelling variations thereof, is used herein to refer to a light conductive element that provides light of the necessary wavelength(s) to be used in connection with the sensors and the system of the present invention. The waveguide allows transmission of light into the patient's body to excite the analyte so that the emitted light can be detected externally, from outside the body.

In the exemplified embodiment of the invention, the refractive index of the analyte solution in the sensor chamber is chosen to be as near, or if possible, substantially identical, to that of the optical fiber, to permit it to become in effect an extension of the optical fiber means for increased efficiency of emitted light transfer through the optical fiber to the detector. Again without intending to limit the present invention to any particular theory, it is known that optical fibers conduct light because the internal refractive index is much higher than that of the environment outside the fiber. For example, the refractive index of air is approximately 1.0, while that of typical optical fiber is about 1.5. This difference means that the fiber collection angle is about 60°. In other words, light approaching the fiber wall from the inside at angles up to 30° (½ the collection angle) is reflected back into the fiber and continues to travel along the fiber. This would also be the case for a thin tube filled with a high refractive index solution, and efficient light guides constructed in this manner are known. See, for example, Oriel Corp., Stratford, Conn. There are many liquids known to possess refractive indices (r.i) high enough for forming light guides, such as, for example, possessing a refractive index higher then about 1.4, e.g., 40%-80% sucrose in water (r.i.=1.40 to 1.49), glycerol (r.i.=1.47) or mineral oil (paraffin oil) (r.i. 1.47) as compared with water (r.i.=1.33) using communication grade acrylic fiber optics with a core refractive index of 1.495 and a collection ('acceptance') angle of 60°.

Suitable plastic for the optical fibers include, e.g., but without limitation, polymethylmethacrylate, or one having a silica light core, which is of a size suitable for entry into a tissue area to be tested. The fiber core diameter for the exemplified laser light is preferably less than 200 microns, whereas for collecting the phosphorescence it is preferably about 400 microns, although diameters from 50 to 1,000 could be used, with diameters of 100, 200, 300, 400, 500, 600, 700, 800, or 900 also used.

In an alternative embodiment, the optical fiber(s) are encased with a sleeve of a biocompatible, but suitably inert material, such as a plastic for a portion thereof before and after leaving the sensor chamber. To provide greater rigidity and durability, the gas-permeable sleeve preferably has a portion which overlaps an end portion of a probe means of a corresponding length, and in which a portion of overlap can be, for example, fusion sealed to form a probe containing at least the gas-permeable layer enclosed sensor chamber. For protection and durability, the end of the probe adjacent to the needle can be reinforced with a plug or other protective covering. See FIGS. 1-3.

3. Sensor Chamber

A small sensor chamber contains a solution of oxygen sensitive analyte, typically within a small diameter tube of a biocompatible, gas-permeable material. A gas-permeable layer, such as a plastic, is selected that neither absorbs the excitation light, nor the phosphorescent light from the sensor. Thus, the selected plastic should have a low solubility for oxygen and a low diffusibility of oxygen. The material(s) of construction of the gas-permeable layer is not critical to practice of the invention, and can be any of the known material, including, but not limited to, such plastic layers as silastic, Teflon™, polyethylene and polypropylene, so long as it does not inhibit gas permeability to the sensor analyte and meets the requirements for the transmitted light. Teflon is used in the exemplified embodiment as described in greater detail below.

The solution containing the aqueous, sensor is further described herein in terms of the phosphorescent analyte, although as indicated below, a fluorescent sensor may also be added to the sensor chamber. Although phosphorescence is emitted uniformly in all directions, in the present invention, the phosphorescent solution preferably has a higher refractive index than that of the gas permeable layer (plastic in the wall of the tube), such that the solution acts as a light pipe or guide. Phosphorescent light, which is emitted at angles less than the collection angle of the light pipe (numerical aperture), is thus refracted back into the solution and along the tube. In other words, because the refractive index of the solution (having a high refractive index core) is higher than that of the wall of the plastic tubing (having a low refractive index core), transmitted light hits the wall at less than the refraction angle. Thus, light is refracted back into the solution.

When optical fibers are used, excitation light is delivered to the sensor solution by the excitation fiber, and is thus channeled down the fiber core, rather than exiting from the sides. This confines the light to the solution (light pipe effect within the gas-permeable tube layer surrounding the sensor and fiber(s)). As a result, the efficiency of exciting the phosphor is greatly enhanced because less light is lost through the wall of the sensor, or of the optical fibers. Moreover, the efficiency of collecting the phosphorescence emitted from the excited phosphor in the sensor chamber is greatly enhanced.

The excitation delivery and collecting optical fibers, respectively, are operably connected and sealed to the proximal end of the sensor tube containing the analyte solution (the probe). In the method of operation of an exemplified embodiment, the excitation light travels along the tube to the phosphor in solution in the sensor chamber, and then following excitation of the phosphor, the oxygen-quenched, emitted phosphorescence light is transmitted back along the tube, where it is collected by the collection optical fiber and delivered to the detector.

There are several embodiments of the tube that would be useful for specific applications. In one embodiment, for example, several fibers are provided for excitation of different lengths of time or wavelengths. The excitation light may be applied through each of the plurality of individual fibers in sequence. In another embodiment, depending on the concentration of the phosphor (absorption of the excitation wavelength), a single collection fiber is used. In the alternative, however, a collection fiber may be provided for each corresponding excitation fiber.

In yet another embodiment, the excitation light may be further confined to a short region of the tube near the end of the fiber for absorption by the phosphor, whereas emitted longer wavelength phosphorescence could travel longer distances through the sensor solution. Thus, the phosphorescence lifetime (equating to oxygen pressure) is measured for each excitation site along the tube. For longer distances the number of collection fibers could be increased as needed, although optimally there is one collection fiber (or fiber site) per excitation fiber (or fiber site).

An exemplified material for covering the sensor tube is Teflon™, in particular Teflon AF™, which is highly permeable to oxygen. The use of the low refractive index Teflon AF™ for the sensor tubing makes the refractive index of water sufficient to produce a good light guide effect. However, other forms of Teflon™, as well as other plastics, could be used. The only requisite criteria are that the oxygen permeability of the tube must be high enough that the sensor solution can rapidly respond to alterations in the oxygen pressure in the tissue ("tissue oxygen pressure"), and that the response is sufficiently rapid for the particular application. In general, the following characteristics each enhance the performance of the sensor: thinner wall; smaller tube; and higher oxygen permeability of the wall material. The effect of each enhancement is cumulative if combined.

4. Extendable/Retractable Insertion Needle

Unless the probe is surgically implanted, the device further comprises a resilient, extendable/retractable insertion needle of a size and shape suitable for use in tissue to facilitate insertion of the sensor probe through the skin and into the patient's tissue. See FIG. 3. For example, the needle is designed to permit insertion of the sensor probe through the skin into the tissue beneath it, including muscle or other dense tissue, or through the abdominal wall into an underlying organ. Such a needle has an inner and outer surface and in one embodiment a round cross-section, but the needle is not limited to a round cross-section, and may be oval, square or otherwise, depending on the shape of the probe. The size of the needle may match the size of the probe and guides its inward motion into and through the tissue, including skin and internal organs.

In any embodiment of the invention, known needle retraction mechanisms may be used, whereby after entry of the probe, the needle guide is retracted from the projecting position to a position posterior relative to the sensor probe tip. The insertion needle for inserting the probe into tissue would be similar to retractable needles already known in the art, e.g., as used for inserting intravenous catheters. A suitable needle retraction mechanism for use in the present invention could be similar to one of those disclosed in U.S. Pat. No. 5,782,804, which is incorporated herein by reference, although it refers to needles for liquid delivery or delivery to a vessel. Retraction may be internal or external, but is preferably external to the probe, and may include one or more elastomeric or resilient ring members to operably seal the sensor probe and the needle member. See, e.g., FIG. 3.

The needle has a central hole larger than the external diameter of the sensor tube containing the oxygen sensitive phosphor solution. The gas-permeable layer covered sensor chamber sits within the needle or extends proximally from the needle during insertion. Such needles typically have an inner diameter within a range of approximately 0.002 inch to 0.010 inch and an outer diameter within the range of approximately 0.004 inch to 0.012 inch. The purpose of the needle is simply to offer protection for the sensor chamber when it penetrates the skin and/or enters the tissue. It adds strength and sharpness, and then is pulled back out of the way, so that it is not directly involved in the system for measuring tissue oxygen concentration. It is used only for transport purposes for the sensor chamber. Practitioners in the medical field are familiar with many similar devices, as used for the leading end of catheters, etc. In a specific embodiment, the needle catheter may include a sensing capability to determine penetration depth of the needle, as well as dial-in needle extension.

5. Oxygen Sensor

The preferred oxygen sensor of the present invention is an oxygen sensitive phosphor according to the design of Vinogradov and Wilson, see e.g., as described in the U.S. Pat. No. 5,830,138, incorporated herein by reference in its entirety. In the preferred construct, the sensor comprises phosphorescent Pd or Pt porphyrins encapsulated in dendrimers to: protect it from quenching agents other than oxygen; and to give it an appropriate quenching constant for oxygen (known in the art). The dendrimer coated porphyrin is then coated with an inert, biocompatible material, such as polyethylene glycol, that would make it fully soluble in aqueous solution contained within the sensor Phosphorescent Compounds or Phosphors: Measurements in the invention are based upon the oxygen quenching of the phosphorescence of a phosphorescent compound having a known quenching constant and known lifespan at zero oxygen for a given temperature. Repeated measurements can be used as a quantitative analysis of the time course of alterations in oxygen content in response to changed conditions. If the quenching constant and lifespan are unknown for a particular phosphor analyte, values can be determined by calibrating the quenching constant and lifetime at zero oxygen.

"Phosphors" or "phosphorescent compounds" of the present invention include any $O_2$-sensitive compound which is soluble in the substrate being tested, and which upon excitation by a selected light source will produce a measurable phosphorescent light. In a homogeneous chamber, such as in the present invention, essentially all of the phosphor in the chamber should have the same lifetime, in contrast to heterogeneous oxygen distributions where information is found in the lifetime distribution. The phosphorescence lifetime of the excited phosphors suitable for the present invention is diminished or reduced ("quenched") by $O_2$. The preferred selected phosphors contained in the sensors are hydrophilic or aqueously soluble, and generally biocompatible. In the aforementioned alternative embodiment of the invention, "fluorophors" or "fluorescent compounds" of any type known in the art may be used in addition to the phosphors or phosphorescent compounds as the sensor analyte in solution to measure $CO_2$ (pH) or $K^+$ levels in the tissue.

The phosphor employed in the present invention is preferably a material having: (1) a substantial sensitivity to oxygen, i.e. phosphorescence with high quantum yields at body temperature; and (2) a suitable phosphorescent lifetime, preferably on the order of from about 0.1 to about 1 m sec to permit measurement. Although not intended to be limiting, suitable phosphorescent compounds include those described in U.S. Pat. No. 5,830,138 and co-pending U.S. Ser. No. 08/137,624, each of which is incorporated herein by reference, and as published in Vinogradov et al., *J. Chem. Soc., Perkin Trans.* 2:103-111 (1995). The phosphorescent compound is selected from the family of chemicals known as porphyrins, chlorins, bacteriochlorin, porphyrinogen, and their derivatives. Preferred porphyrins of the present invention include those hydrophilic compounds having the following formula:

wherein R1 is a hydrogen atom or a substituted or unsubstituted aryl; R2 and R3 are independently hydrogen or are linked together to form substituted or unsubstituted aryl; and M is a metal. In certain preferred embodiments, M is a metal selected from the group consisting of Zn, Al, Sn, Y, La, Lu, Pd, Pt and derivatives thereof. Examples of such porphyrins, while not intended to be limiting, include, e.g., tetrabenzoporphyrin, tetranaphthoporphyrin, tetraanthraporphyrin, and derivatives thereof. More specifically, examples of applicable porphyrins, include, e.g., meso-tetraphenylated derivatives; tetraphenyltetrabenzoporphyrins; tetraphenyltetranaphthoporphyrins; meso-tetra-(4-carboxylphenyl) porphyrins; meso-tetraphenyltetrabenzoporphyrins; meso-10 tetraphenyltetranaphthoporphyrins; and tetrabenzoporphyrins.

In connection with the preferred substituted compounds of the invention, the inventors have found that substituent groups impart desirable properties to the compounds. For example, compounds which comprise substituent groups are characterized by solubility in polar solvents, including aprotic solvents, such as dimethylformamide (DMF), acetone and chloroform ($CHCl_3$), and protic solvents, such as water. The degree of substitution and the nature of the substituent groups may be tailored to obtain the desired degree of solubility and in the desired solvent or solvent mixture. The substituent groups are preferably substituted on the chromophobic portion of the compounds of the invention. The term "chromophobic portion" includes, for example, the atoms in the compound of formula I which are immediate to the porphyrin moiety, as well as the R1, R2 and R3 groups. Preferably, the substituent groups do not negatively affect or alter the absorbance and/or emission characteristics of the chromophores.

More specifically, for use in the present invention, are known dendritic derivatives of the aforementioned porphyrin phosphors, which are highly efficient and highly soluble phosphorescent compounds surrounded by an inert globular structure. An example of such a compound is a derivatized metallotetrabenzoporphyrin compound, such as the Pd-complex of Pd-tetrabenzoporphyrin or Pd-meso-tetra-(4-carboxyphenyl) porphyrin. As disclosed in the U.S. Pat. No. 4,947,850, incorporated herein by reference, substituent groups are known to impart desirable properties, such as solubility, to the preferred phosphorescent compounds. Formulation of preferred aqueous phosphorescent compounds of the present invention is provided in detail in the '138 patent, which is herein incorporated by reference.

The preferred porphyrin structures are surrounded by a three-dimensional supramolecular structure known as a dendrimer. It is known that one-, two-, and three-layer polyglutamate dendritic cages synthesized divergently around novel derivatized extended metalloporphyrin, oxygen-measuring, phosphor compounds provide phosphors which are highly water-soluble in a wide pH range and display a narrow distribution of phosphorescence lifetime in deoxygenated water solutions.

The phosphor-containing sensor solution is exposed to a modulated light source capable of exciting the phosphor to emit phosphorescent light, which permits measurement and calibration of both the phosphorescence intensity and delay time between the excitation light intensity and the phosphorescence emission (signal). Therefore, accurate determination of the frequency dependence of the signal amplitude and phase is used to calculate the oxygen pressure histogram of the sample using algorithms. The measured oxygen pressure histogram can then be used to accurately calculate the oxygen concentration gradient throughout the sample.

Phosphorescence quenching has been thoroughly verified as a method of measuring the oxygen dependence of cellular respiration (see, for example, Vanderkooi and Wilson, "A New Method for Measuring Oxygen Concentration of Biological Systems, in *Oxygen Transport to Tissue VIII*, Longmuir, ed., Plenum (August 1986); Vanderkooi et al., *J. Biol. Chem.* 262(12):5476-5482 (April 1987); Wilson et al., *J. Biol. Chem.*, 263:2712-2718 (1988); Robiolio et al., *Am. J. Physiol.* 256 (6 Pt 1):C1207-1213 (June 1989); Wilson et al., *Adv. Exp. Med. Biol.* 316:341-346 (1992); and Pawlowski et al., *Adv. Exp. Med. Biol.* 316:179-185 (1992). For detailed data on the calibration techniques and oxygen measurement capabilities of one widely used phosphor, see Lo et al., *Analy. Biochem.* 236:153-160 (1996). At constant temperature, phosphorescence lifetime is independent of the other parameters and composition of the sample.

It is important in the present invention to use a compound of known quenching constant and known lifetime at zero oxygen for a given temperature. Thus, once the compound and temperature are determined, calibration need only be made on a single occasion, after which the value can be used for all subsequent measurements involving that compound. Measurements according to the present invention are rapid and highly reproducible. Less than 2 seconds are required for each measurement and current instruments have a measurement-to-measurement variability of less than 1 part in 1000. Due to the absolute calibration, equally low variability is attained among different tissue samples having the same oxygen pressure.

Excitation of the Phosphor(s):

In accordance with the invention, a light source means, preferably a modulated light source, is employed for excitation of the soluble phosphor compound in the sample to a state of phosphorescence. The designs of the light source and/or detector, in accordance with this invention, are not critical to the practice of this invention and may take any suitable form employing any conventional and non-conventional components. A beam of excitation light is passed through the sensor solution from any direction, but as embodied, through the light tube, so long as the beam passes completely throughout the sensor. The emitted phosphorescence is then collected from any point, but as embodied, through the light tube.

Phosphorescence lifetime measurements use modulated excitation light, i.e., undulated sinusoidally, from 20 to 50,000 Hz, preferably from 50 to 35,000 Hz, most preferably from 100 to 20,000 Hz. The preferred measurements detect only those emissions that are at a longer wavelength and modulated at the same frequency.

The light source means can be provided by any of several different sources, including a flash lamp, a pulsed light emitting diode, or a pulsed laser. In one exemplified embodiment, the excitation light is applied as a flash of monochromatic light (a width at half-maximal intensity of less than 5 microseconds for flashlamps), filtered to provide the desired wavelength, i.e., between 400 and 700 nanometers. In another exemplified embodiment, the light source is a light-emitting diode (LED), such as a laser diode. LEDs provide monochromatic light with a relatively broad bandwidth. Such light is passed through an interference filter, thus blocking the long wavelength "tail" in the emission of the LED, which might otherwise interfere with fluorescent measurements of the present invention. The separation of excitation and emissions wavelengths of oxygen-quenchable phosphors is generally sufficient to not require such a filter. Ideally, all light emitted from an LED or laser diode (LD) would be at the peak wavelength, but in practice light is emitted in a range of wavelengths centered at the peak wavelength. This range is referred to as the "spectral width" of the source.

Solid state light sources can be readily modulated at the desired frequency and are monochromatic, i.e., light emission occurs primarily in either a broad band up to about 60 nm bandwidth at half-height for LEDs, or at a narrow band of 1 nm or less for laser diodes. As a result, minimal optical filtering is required for optimal application of such light to the measurement of phosphorescence lifetime levels. Modulation of the light can be achieved either by direct modulation of the light source or by passing the light through a modulation device, such as a flasher or a rotating wheel with slots through which the light may pass.

Measuring the Emitted Phosphorescence:

Measurements of the present invention are readily adapted for low levels of oxygen, such as would be found in hypoxic tissue. The present optical method is not dependent on sample path length or light scattering.

Measurements of phosphorescence lifetime are independent of the concentration of the phosphor(s) in the sensor solution, so long as the phosphor(s) is present in the solution at a concentration range needed for oxygen measurement. Within the functional concentration range, there is no significant "self-quenching" due to energy transfer from triplet state to ground state phosphor molecules. This is because of the relatively large size and charge of the preferred dendrimer phosphor constructs. Measurement of phosphorescence lifetime is also independent of absorption by other chromophores, such as hemoglobin, which may be present in the tissue. Lifetime measurements are independent of changes in absorption and light scattering, as long as the changes do not occur during phosphorescence decay (<1 msec). This makes the method particularly effective in measuring oxygen in sample conditions affected by contaminants, such as blood, dyes or other colored components within the tissue.

Based upon the principle that the beam of excitation light passed through the environment will equally excite the phosphors in the sensor solution at all levels, and because the phosphorescence lifetime increases as the oxygen concentration in its immediate environment decreases, the calculated values are necessarily greater for points of lower oxygen concentration. Phosphorescence may be measured by any available means in accordance with the present invention.

Measuring Phosphorescence:

In general, two conventional methods for measuring phosphorescence lifetime (or decay time) are (i) the "pulse method" in the time domain, and (ii) the "phase method" in the frequency domain. The exemplified embodiments of the present invention are based upon applications of the phase method, although both may be used, and in the art are considered to be equally effective.

In the pulse method embodiment, the phosphor is excited by a short pulse of light and the resulting phosphorescence emission in the longer wavelength is an exponentially decaying function with a measurable rate of decline. The pulse method is used in the majority of existing instruments for oxygen measurement.

By comparison, in the preferred phase method embodiment, the phosphor solution is excited with modulated light, with absorbed light being re-emitted as phosphorescence after a certain delay period. As a result, phosphorescent emission is also modulated with the same frequency, but delayed in time (phase shifted) with respect to the excitation wave. The resulting phase shift, found experimentally, is used to calculate the emitted phosphorescence lifetime.

The phase method embodiment is preferably used because frequency lock amplification can be advantageously used to greatly increase sensitivity. It also allows use of much lower intensity and more durable light sources, which can be of significant advantage with respect to long term stability and reliability of the instruments. Interference from ambient light is greatly decreased by this method, since only signals with the same modulation frequency as the excitation light are amplified, which largely eliminates interference by other ambient light sources.

The phosphorescence lifetime measurements and calculations may be fully automated in certain embodiments of the invention. The values of the phosphorescence intensities and lifetimes may also be recorded or tabulated for later analysis, and the measurements may be repeated as often as necessary until the desired endpoint is reached. The time point at which each data point is measured is recorded, from which the oxygen concentration can be calculated. Measurement of the phosphorescence lifetime is extremely reproducible from instrument to instrument, due partly to the absolute calibration and partly to the nature of the lifetime measurements.

Phosphorescence Detection:

In practice of an embodied method of the invention, following excitation, phosphorescence is collected, optionally passed through appropriate filters, and carried to the recording apparatus of the present invention to obtain the phosphorescence lifetime measurements and calculated oxygen pressure using the relationships disclosed below, e.g., Eq. 1. See. FIG. 3. Photodetection devices are well understood and readily used in the art, and further discussion of the phosphorometer photodetector (PD) is not believed to be necessary for the practice of the present invention by the skilled practitioner. All are herein included, e.g., photomultipliers, photodiodes, including silicon PIN photodiodes with a built-in preamp, and avalanche photodiodes (APD), including silicon APD. With respect to partial pressure oxygen measurement, a sine wave signal of the desired frequency can be generated by a digital signal processor (DSP) system for digitizing and quantifying a phosphorescence signal, including determination of a phase shift relative to the light output of the LED and of the phosphorescence signal magnitude.

The phosphorometer photodetector output is amplified to provide a signal of optimal voltage for digitizing by the analog-to-digital converter (ADC). A photodiode with an internal amplifier is selected for the optimal light sensitive surface area and lowest noise level. For example, the Hamamatsu Corporation HC120 analog photomultiplier tube assembly with an R3823 photomultiplier has an appropriate surface area (more than 5 mm$^2$) and excellent photosensitivity, in the 500 v to 900 nm wavelength range, as manufactured by Hamamatsu Photonics, KK of Hamamatsu, Japan.

In one embodiment of the present invention, the emitted light is filtered and detected with an avalanche photodiode. The output of the detector is amplified and passed to a 16 bit (or greater) ADC, e.g., but not limited to, a Delta-Sigma digitizer operating at 48 or 96 kHz. This signal is used to control the current in the LED driving circuit. The LED driver circuit is preferably designed to provide greater than 90% modulation of light output by adding a DC signal to the sinusoidal signal, such that the minimum current is just above the threshold for light emission. Above this threshold light output is nearly a linear function of the current through the LED.

The signal from the photodetector may be further amplified with an AC-coupled operational amplifier. In an embodiment using a continuously modulated light source, a phase lock amplifier system could be used to determine the decay (phase shift) between the excitation and fluorescence and thereby the phosphorescence decay constant ("lifetime"). The measurements could be repeated as rapidly (up to 40 to 100 times per second) or as slowly (once every few minutes) as needed. The present invention thus provides stable measurements of oxygen pressure over extended periods of time. The quality of the phase detection depends on the reduction of noise level in the photodiode output signal.

The measured values of oxygen pressure can be presented in any form the user desires, for example, after amplification, the output signal is delivered to the analog multiplexer and then input into the analog-to-digital converter (ADC) for digitizing. Data collection from the digitizer is synchronized with readings of the tabulated values into the digital-to-analog converter (D/A unit) providing the driving current for the light source. Data collection is always begun at the same point in the table of values controlling the light output, e.g., the LED light output.

As embodied, the digitized phosphorescence data is transferred to a specific file in memory, preferably a 1024×32 bit block of memory. Further data sets (a total of m data sets) are added to the same memory area, always beginning at the same point. Because the collected data are "locked" to the table of values being used to control the excitation light, only signals of exactly the same frequencies as those used to generate the excitation signal are summed positively. All other signals (and noise) are summed destructively, and their amplitudes decrease as the number of scans (m) increases. Noise amplitude, on the other hand, increases only as the square root of the number of scans summed (m½), thus providing increase in signal-to-noise ratio. In an exemplified configuration, 20 data sets are summed. Assuming that each data set is approximately 20 msec long (1024 points at 48 kHz), summing the 20 sets would require less than 0.5 seconds.

Quenching of phosphorescence lifetime by oxygen is determined by the frequency of collisions between the excited triplet state molecules and oxygen. This means the measured phosphorescence lifetime may be converted to oxygen pressure according to the Stern-Volmer relationship, which is stated as follows:

$$\tau_o/\tau = 1 + k_q \tau_o \cdot PO_2 \tag{Eq. 1}$$

where $\tau_o$ and $\tau$ are the phosphorescence lifetimes in the absence of oxygen, $PO_2$ is the oxygen pressure for a lifetime of $\tau$, and $k_q$ is the quenching constant. The quenching constant $k_q$ is related to the frequency of collisions between the excited triplet state molecules and the oxygen molecules and the probability that energy transfer will occur in any given collision. Use of the Stern-Volmer relationship is also set forth in U.S. Pat. No. 5,501,225, which is herein incorporated by reference.

Mathematical Relationship between Phase Shift and Phosphorescence Lifetime:

In the phase approach, the mathematical relationship between phase shift and phosphorescence lifetime can be described as follows:

$$\tan \phi = 2\pi f t \tag{Eq. 2}$$

where $\phi$=phase difference (phase shift) between excitation and emission sine waves at the modulation frequency, f and t=lifetime of phosphorescent decay.

It can be shown that for a given signal-to-noise ratio, the lowest error in the estimation of the phosphorescence lifetime is obtained when the phase shift is about 26°.

It follows from the Stern-Volmer relationship and the diffusion equation that to maintain the phase shift of about 26° for all oxygen concentrations in the range, it is necessary to be able to vary the modulation frequencies from 20 Hz to 20,000 Hz. However, it is preferred that modulation frequencies be controlled from 100 Hz to 20,000 Hz, and instrumentation may be employed which can measure phosphorescence lifetime of a given fixed frequency and/or at a first estimate optimal frequency for a given value of the phase shift (35.5°), and to then proceed with actual lifetime measurements. To ensure oxygen measurements are accurate to air saturation and above (lifetimes as short as <15 μsec), the phosphorescence signal is preferably sampled (digitized) at 48 kHz or greater.

The digital signals are processed to extract the signal strength (magnitude) and phase relative to the excitation light. Calculations of the phosphorescent lifetime and oxygen pressure will follow the above-described procedures.

Overall, the system must be rapidly responsive, small, and capable of being stored for long periods, yet maintain the ability to rapidly respond throughout storage, so that it is ready when required. Preferably, the system is capable of operating from a battery source for several hours, making it easily portable. Moreover, the electronic parts should be no larger than a handheld PDA device to make the portability useful.

The method of using the disclosed system and probe generally comprises the steps of selecting a site where measurement of the patient's tissue oxygen is needed and determining where the system should be introduced into the patient to place the sensor in the tissue at the desired location. The method continues by contacting the patient with the sensor and optical fiber-containing probe, thereby equilibrating the tissue oxygen with the analyte through the gas-permeable layer surrounding the sensor chamber; emitting excitation light from the light source into the optical fiber whereby it is transmitted to and excites the phosphor and/or fluorophore analyte within the sensor chamber; collecting the emitted light from the analyte and returning it via at least one optical fiber to the detection device means (which may include amplifying the signal and other factors described as part of the system); detecting phosphorescent and/or fluorescent emissions from said oxygen quenching and/or pH sensor with the detection device; and calculating the measured tissue oxygen and/or pH based on the results of the detecting step. The measured oxygen pressures are closely correlated with the oxygen pressure in the capillary bed in the tissue and provide a measure of the integrated function of the performance of the cardio-pulmonary system. The measurements provided by the present invention are valuable assets in clinics, in intensive care units, in the care of soldiers in the field and in emergency care units.

6. Alternative Embodiments

In an alternative embodiment of the invention, a device like the one described above is used, but instead of connecting to an optical fiber in the probe for transmitting the excitation light to the sensor analyte, those fibers and connections are removed—creating a wireless system. In this alternative embodiment, the sensor molecules would be selected to have absorption and emission bands in the near infrared region of the spectrum (absorption between 600 nm and 850 nm and emission between 630 nm and 1300 nm). The selected light source, such as an LED, could then be placed on the patient's skin in closest proximity to the tube inserted or implanted in the patient's tissue up to 1 or 2 cm deep in the tissue, wherein the tube contains the gas-permeable layer covered, analyte-filled sensor chamber (the probe element of the system). In other words, the optical fibers for the excitation light are replaced by the near infrared emitting LED that transmits the light transdermally through the patient's skin. Similarly, to permit the removal of all outside connections to the probe, the remaining collection optical fibers for transmitting the analyte-emitted light to the detector are also removed from the present system. Instead, the detection device (CCD or equivalent) are place on the surface of the patient's skin in closest proximity to the probe element of the system. This embodiment relies on the ability of near infrared light to penetrate substantial thicknesses of tissue due to the low level of absorbing pigments at these wavelengths.

In practice, the light from the LED penetrates the patient's skin and surface tissue, striking the analyte filled tube or probe and exciting the analyte to produce measurable levels of oxygen quenched phosphorescence and/or pH-indicating fluorescence. Then in a reverse process, the emitted phosphorescent and/or fluorescent light is returned to through the patient's surface tissue and skin to the detector device. An adequate signal is transmitted by measuring for low phosphorescence levels, by using a sufficiently high concentration of phosphor in the sensor chamber, by using a bright LED to produce the excitation light, and by keeping the sensor tube within less than 1 cm or not more than 2 cm of the skin surface or outer surface of an organ, muscle, or whatever tissue is being analyzed. Such a wireless, surface system for measuring tissue oxygen would be particularly effective for use for resuscitation and emergency care, although it may not be ideal for all situations, and the full system may offers broader application. In one aspect of this embodiment, the excitation and emission light can independently pass through thicknesses of one or more centimeters of skin or tissue if the excitation light is delivered wirelessly and transdermally, from outside of the patient to a probe positioned within the tissue.

In a second alternative embodiment, also using sensor molecules that absorb and emit in the near infrared, uses oxygen sensors that are encapsulated in physiologically-acceptable polyethylene glycol (PEG). The PEG encapsulation has recently been approved by the FDA for human use, although before clinical use, the selected phosphor would also have to be approved. Thus, the PEG encapsulation replaces the gas-permeable film over the analyte, and when combined with the placing the light source and detector on the skin surface, would permit the PEG encapsulated sensor to be directly injected into the patient's tissue, such as muscle, preferably at depths of less than 1 cm or not more than 2 cm to make measurements easier. Such intramuscular injections of PEG encapsulated phosphors have been shown to distribute into the interstitial space within the tissue and remain there for several hours without washing away in a tissue environment, thus accurately reporting the oxygen pressure in the tissue. Only a few micrograms of the injected PEG-coated sensor would be required, and then the analyte could be excited from the skin surface and detected as describe for the wireless, surface system above. Such a system, once approved would offer a simple, effective, inexpensive and highly portable method for rapidly measuring tissue oxygen, and may eventually become the preferred method of choice, particularly for emergency purposes.

In another alternative embodiment, as mentioned above, in addition to tissue oxygen, $pH(CO_2)$, or even $K^+$, is directly measured in the tissue by the response of a fluorescent indicator in the sensor chamber, which fluoresces at the same wavelength, but absorbs at different wavelengths in the acid and base forms. For example, a mechanical adaption can be constructed which optimizes assembly of the LED, interference filter and of an optical filter fibrous light guide, which can be connected to a fiber optic switch to send the beam as either, or both, excitation for the phosphor and/or fluorphor, or to a photodiode detector to measure relative intensities of analyte excitation at multiple wavelengths. This allows the ratio of the fluorescence at the two different excitation wavelengths to be used as a measure of pH, which provides a measure of the $CO_2$ concentration in the tissue. As long as the relative intensities of excitation light of the two different wavelengths is known, the measured pH values are independent of the concentration of fluorophor, the intensity of the excitation light, and the efficiency of collection of the emitted fluorescence. The measured excitation energies are used to correct the fluorescence intensity ratio for the equal energy of the two wavelengths. After switching, excitation light can be passed into a 50:50 coupler with a common end terminated with a connector designed for rapid and reproducible connection of a fiber optic means, for example, connected to the sensor chamber.

In yet another embodiment of the invention, at least a portion of the optical fiber(s) at the point where the sensor chamber is operably connected within the gas-permeable layer seal, is faceted, etched, or configured to have a plurality of scratches, depressions, grooves, pitting or otherwise, holes and the like. As a result, emitted phosphorescence has an increased probability of being collected by the fiber for return to the detector. In effect, the phosphor solution in the chamber, as a result of the grooves, etching, etc. becomes a part of the optical fiber. Each of the plurality of grooves is not more than 20% of the fiber diameter in depth, to allow for sufficient fiber strength, while at the same time allowing for the phosphor solution to penetrate well into the fiber. Such etching may substantially increase the probability of phosphorescence entering the fiber within the collection angle.

To illustrate the effectiveness of the present oxygen monitoring device, several clinical applications are provided in the following examples, but while exemplary, they are not intended to in any way limit the breadth of the invention which is, in fact, limited only by the breadth of the claims defining the invention.

EXAMPLES

There are several clinical situations in which the ability to monitor delivered oxygen to specific tissues on a real time continuous basis would help improve patient care. These include, without limitation, patients who: 1) have undergone abdominal surgery for ischemic bowel, 2) have had a surgical muscle flap created, especially a free flap, and 3) those who have a need for cardiopulmonary resuscitation, since prior art methods for monitoring oxygen levels in the patient in each situation is inadequate.

Example 1

Monitoring of an Ischemic Bowel

Pediatric and adult patients can develop conditions, such as volvulus, necrotizing enterocolitis and strangulation of the intestine due to an adhesion. These cause regional ischemia of the intestine requiring an exploratory laparotomy and possible resection. Often there are areas of the intestine that are transition zones with potential viability. To help preserve as much of the intestine as possible a second (or third) surgical look may be required to assess these areas. Further, there is no way to judge the outcome of therapies to improve intestinal viability until it is reassessed visually. Computerized tomography is of limited use and usually cannot distinguish viable from non-viable tissue, except at the irreversible extreme. Plain X-rays are also only useful at the extreme, when perforation has occurred due to tissue necrosis.

Solution Using Present Invention:

Following the initial laparotomy, the surgeon can, in accordance with the present invention, place an oximeter catheter, within or attached to a surgical drain(s) in the area of concern. Also, one may have multiple individual fiber optic bundles monitoring areas spaced along the length of the catheter. Further, a lattice could be created with the catheter material that could monitor the two-dimensional areas As further set forth in U.S. Pat. No. 6,274,086, herein incorporated by reference, two- and three-dimensional oxygen imaging of tissue is accomplished by measuring phosphorescence emission of the oxygen-quenchable compounds in an apparatus comprising a matrix of light guides and/or phosphorescence detectors to allow precise and sequential introduction of pulses of excitation light from a plurality of sites in the matrix. As a result, if ischemia is detected, the clinician can rapidly consider strategies to improve perfusion while the bowel is still viable and accessible, before necrosis makes repair impossible.

Example 2

Monitoring of a Muscle Flap

As part of restorative surgery to fill in a space created by re-section of diseased tissue or loss from trauma, surgeons often mobilize muscle from one area and transfer it to another. This muscle may still have its native vascular supply intact, or it may be completely disconnected, in which case it is reattached to another vascular supply (free flap). Such surgery is often complicated by flap failure due to an inadequate vascular supply, and unfortunately, it is often difficult to monitor the integrity of the flap because it is subcutaneous. Doppler ultrasound may be used, but it can only determine whether a pulse can be detected in or near the tissue.

Solution Using the Present Invention:

An oximeter catheter of the present invention could be inserted along the body of the flap or inserted into the body of the muscle, and the integrity of the muscle can then be monitored at various points on the flap while in situ. This could be easily removed along with surgical drains once the condition of the flap has been insured, or at the time of a second operation. As a result, if ischemia is detected, the clinician can consider strategies to improve perfusion while the flap is still viable, and as above, before necrosis has caused irreversible damage.

Example 3

Monitoring Cardiopulmonary Resuscitation

The American Heart Association has established guidelines for providing cardiopulmonary resuscitation (CPR) to victims of cardiac or respiratory arrest. One of the difficulties in providing this potentially life saving care, is the inability to monitor in real time, the adequacy of chest compressions and the delivery of oxygen into the tissues of the patient. In an intensive care unit a patient may have an arterial line already established, permitting medical practitioners to periodically sample the patient's blood to monitor progress. However, before the patient reaches the ICU, arterial lines are not used because they take time and expertise to establish, making them impractical to use in an acute situation. As a result critical measurements of tissue oxygen are not possible.

Solution Using the Present Invention:

At initiation of CPR, one could insert the oximeter catheter into a deltoid, masseter or other muscle as a surrogate for cerebral perfusion and/or oxygenation. One could monitor delivered oxygen to those tissues on a continuous basis during CPR, and thus monitor the quality of the resuscitation in critical tissues.

The disclosures of each patent, patent application and publication cited or described in this document are hereby incorporated herein by reference, in their entirety. However, the disclosed dates of publication may be different from the actual publication dates, which may need to be independently confirmed. No reference identified herein is to be construed as an admission that the present invention is not entitled to antedate such publication by virtue of prior invention.

While the foregoing specification has been described with regard to certain preferred embodiments, and many details have been set forth for the purpose of illustration, it will be apparent to those skilled in the art, that without departing from the spirit and scope of the invention, the invention may be subject to various modifications and additional embodiments, and that certain of the details described herein can be varied considerably without departing from the basic principles of the invention. Such modifications and additional embodiments are also intended to fall within the scope and spirit of the invention appended claims.

What is claimed is:

1. A system for detecting and measuring oxygen directly in muscle of a patient, the system comprising:
    a probe comprising:
        a sensor chamber enclosed within a biocompatible, gas-permeable layer; and contained within the sensor chamber, an oxygen quenchable, aqueously-soluble, oxygen sensor comprising a phosphor solution that upon excitation emits phosphorescence, wherein refractive index of the solution in the sensor chamber is higher than that of the surrounding gas permeable layer, enhancing internal reflection, and causing the phosphorescent light to be channeled within the liquid core, rather than exiting from the sides of the probe, wherein the probe has a wall-strength to withstand external pressure within muscle, thereby allowing the probe to be suitable for insertion directly into muscle;
    a light source for transmitting controlled excitation light to the phosphor solution; and
    a detecting device for detecting light emitted from the excited phosphor.

2. The system of claim 1, further comprising two or more aligned optic fibers, each having two opposing ends, and each of which is operably connected and sealed at the distal end to the probe and the connection is enclosed within the gas-permeable layer of the sensor chamber, thereby forming an operably-linked light guide for collecting the phosphorescence light emitted at less than the numerical aperture of the light guide; wherein at the proximal end, at least one first aligned optic fiber is externally, operably-connected to the light source to transmit excitation light to the phosphor solution, and wherein at least one second aligned optic fiber is externally connected to the detecting device to collect and transmit light emitted from the phosphor and to transmit it to the detector device.

3. The system of claim 1, further comprising within the sensor probe a fluorescence-emitting pH sensor for directly determining $CO_2$ levels in the surrounding tissue.

4. The system of claim 1, wherein within the probe, the gas-permeable layer comprises a layer of physiologically-acceptable PEG.

5. The system of claim 1, wherein within the probe, the oxygen sensor solution comprises an absorption band having a wavelength greater than about 380 nm.

6. The system of claim 1, wherein within the probe, the excited phosphor sensor emits an emission band having a wavelength greater than about 500 nm.

7. The system of claim 1, wherein within the probe, the absorption and emission bands range from about 400 nm to about 1500 nm.

8. The system of claim 1, comprising the oxygen quenchable sensor phosphor, which is capable of phosphorescence, having the formula:

wherein: $R_1$ is substituted or unsubstituted aryl; $R_2$ and $R_3$ are independently hydrogen or are linked together to form substituted or unsubstituted aryl; and M is $H_2$ or a metal.

9. The system of claim 8, wherein the oxygen sensor compound, M, comprises a metal selected from the group consisting of Zn, Al, Sn, Y, La, Lu, Pd, Pt, LuOH, YOH, LaOH and AlOH.

10. The system of claim 8, wherein $R_2$ and $R_3$ of the oxygen sensor compound are linked together to form an aryl.

11. The system of claim 10, wherein the aryl comprises phenyl, naphthyl or anthryl.

12. The system of claim 8, wherein $R_1$ comprises substituted phenyl.

13. The system of claim 12, wherein the substituted phenyl comprises Pd-meso-tetra-(4-carboxy-phenyl) porphyrin.

14. The system of claim 1 further comprising an excitation fiber to provide excitation light to the phosphor in the probe by the excitation fiber.

15. The system of claim 1, further comprising within the probe a fluorescence-emitting pH sensor for directly determining $CO_2$ levels in the surrounding tissue.

16. A method for detecting and measuring oxygen directly in tissue of a patient by the system of claim 1, the method comprising:
    directly contacting the patient's tissue with the probe device;
    delivering excitation light to the phosphor solution within the sensor chamber of the probe;
    detecting and measuring oxygen-quenched phosphorescence of the light emitted from the excited phosphor; and
    quantifying tissue oxygen concentration from the measured phosphorescence.

17. The method of claim 16, further comprising measuring tissue $CO_2$ levels, wherein the probe further comprises a fluorescence emitting, pH sensor.

18. The method of claim 17, further comprising calculating tissue $CO_2$ levels based on measured pH.

19. The method of claim 16, further comprising monitoring oxygen supplied to the patient's ischemic bowel.

20. The method of claim 16, further comprising monitoring tissue oxygen supplied to the patient's surgically transplanted muscle flap.

21. The method of claim 16, further comprising monitoring oxygen supplied to the patient's tissue during cardiopulmonary resuscitation.

22. A system for detecting and measuring oxygen directly in muscle of a patient, the system comprising:
    a probe comprising:
        a sensor chamber enclosed within a biocompatible, gas-permeable layer; and contained within the sensor chamber, an oxygen quenchable, soluble, oxygen sensor comprising a phosphor solution that upon excitation emits phosphorescence, wherein refractive index of the solution in the sensor chamber is higher than that of the surrounding gas permeable layer, enhancing internal reflection, and causing the phosphorescent light to be channeled within the liquid core, rather than exiting from the sides of the probe, wherein the probe has a wall-strength to withstand external pressure within muscle, thereby allowing the probe to be suitable for insertion directly into muscle;

a light source for transmitting controlled excitation light to the phosphor solution;

a detecting device for detecting light emitted from the excited phosphor; and a retractable insertion needle.

23. The system of claim 1, wherein the oxygen sensor comprises an oxygen sensitive phosphor.

24. The system of claim 23, wherein the oxygen sensitive phosphor comprises a porphyrin.

25. The system of claim 24, wherein the porphyrin comprises metalloporphyrin.

* * * * *